(12) United States Patent
Pfaendler et al.

(10) Patent No.: US 9,969,737 B2
(45) Date of Patent: *May 15, 2018

(54) FLUORESCENT CARBAPENEMS

(71) Applicant: Hans R. Pfaendler, Stockdorf (DE)

(72) Inventors: Hans R. Pfaendler, Stockdorf (DE); Gregor Golz, Augsburg (DE)

(73) Assignee: Hans Rudolf Pfaendler, Stockdorf (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/056,035

(22) Filed: Feb. 29, 2016

(65) Prior Publication Data

US 2016/0251356 A1    Sep. 1, 2016

Related U.S. Application Data

(63) Continuation of application No. 13/806,840, filed as application No. PCT/EP2011/003311 on Apr. 7, 2011, now Pat. No. 9,296,752.

(30) Foreign Application Priority Data

Jul. 8, 2010    (EP) .................................. 10007041

(51) Int. Cl.
| C07D 477/14 | (2006.01) |
| C12Q 1/34 | (2006.01) |
| C12N 9/86 | (2006.01) |

(52) U.S. Cl.
CPC ............ *C07D 477/14* (2013.01); *C12Q 1/34* (2013.01); *G01N 2333/968* (2013.01); *G01N 2333/986* (2013.01); *G01N 2500/00* (2013.01)

(58) Field of Classification Search
CPC .......... C07D 519/00; C12Q 1/34; C12Q 1/18; C12N 9/86
USPC .............. 435/18; 514/300; 540/302
See application file for complete search history.

(56) References Cited

U.S. PATENT DOCUMENTS

| 5,004,740 A | 4/1991 | DiNinno et al. |
| 5,182,385 A | 1/1993 | DiNinno et al. |
| 5,328,904 A | 7/1994 | DiNinno et al. |
| 8,440,424 B2 | 5/2013 | Thrippleton et al. |

FOREIGN PATENT DOCUMENTS

| EP | 0 479 574 | 4/1992 |
| EP | 0 481 662 | 4/1992 |
| EP | 1 251 134 | 10/2002 |
| GB | 2301820 | 12/1996 |
| WO | WO-90/05119 | 5/1990 |
| WO | WO-2009/095258 | 8/2009 |

OTHER PUBLICATIONS

Queenan et al. Clin. Microbiol Rv 2007, pp. 440-458).*
Carvalhaes et al. British Soc. Antimicrobial Chemotherp 2009,pp. 249-251.*
Guthikonda et al., "Structure-Activity Relationships in the 2-Arylcarbapenem Series: Synthesis of 1-Methyl-2-arylcarbapenems", Journal of Medicinal Chemistry, vol. 30, No. 5, pp. 871-880 (1987).
International Search Report dated Nov. 18, 2011, in corresponding PCT Application No. PCT/EP2011/003311.
Written Opinion dated Nov. 18, 2011, in corresponding PCT Application No. PCT/EP2011/003311.
International Preliminary Report on Patentability dated Oct. 1, 2012, in corresponding PCT Application No. PCT/EP2011/003311.

* cited by examiner

*Primary Examiner* — Robert B Mondesi
*Assistant Examiner* — Mohammad Y Meah
(74) *Attorney, Agent, or Firm* — Locke Lord LLP; Nicholas J. DiCeglie, Jr.

(57) ABSTRACT

Chromogenic or fluorescent carbapenems according to formula I, wherein Ar is a mono or disubstituted carbocyclic aromatic group or an optionally mono or disubstituted heterocyclic aromatic group, are useful compounds for the detection of bacterial carbapenemase.

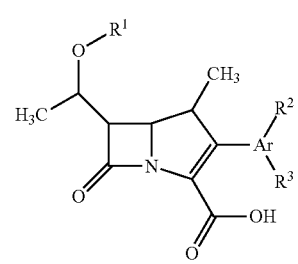

(I)

14 Claims, No Drawings

FLUORESCENT CARBAPENEMS

CROSS-REFERENCE TO RELATED APPLICATIONS

This application is a Continuation of U.S. patent application Ser. No. 13/806,840, filed Dec. 24, 2012, which application is the U.S. national phase application pursuant to 35 U.S.C. § 371 of PCT International Patent Application No. PCT/EP2011/003311, filed Jul. 4, 2011, which claims priority to European Patent Application No. 10007041.6, filed Jul. 8, 2010. The contents of the foregoing applications are incorporated herein by reference in their entireties.

DESCRIPTION AND BACKGROUND OF THE INVENTION

This invention relates to fluorescent or chromogenic carbapenems of formula I

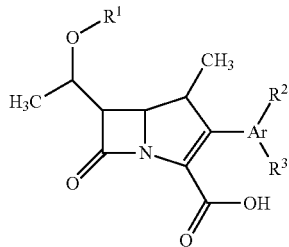

and/or their salts, wherein $R^1$ is selected from hydrogen or alkyl and acyl, each with 1 to 6 carbon atoms and wherein Ar is a mono or disubstituted carbocyclic aromatic or an optionally mono or disubstituted heterocyclic aromatic group wherein the carbocyclic aromatic moiety is monocyclic, bicyclic or tricyclic with 6 to 14 carbon atoms and the heterocyclic aromatic moiety is monocyclic, bicyclic or tricyclic and contains 1 to 13 carbon atoms and contains 1 to 5 hetero atoms, which are selected, independently from each other, from oxygen, nitrogen or sulphur and wherein the substituents $R^2$ and $R^3$ of the aromatic parts Ar are selected, independently from each other, from hydrogen, amino, hydroxy, oxo, fluoro, chloro, bromo, nitro, cyano, carboxy, carbamoyl, sulfamoyl, amidino, guanidino, sulfo or alkyl, alkoxy, acyl, acylamino, monoalkylamino, dialkylamino, trialkylammonium, N,N-dialkylcarbamoyl, N-alkylcarbamoyl and alkoxycarbonyl, each with 1 to 6 carbon atoms.

More preferred, the invention relates to fluorescent or chromogenic carbapenems of formula I, characterized in that the carbocyclic aromatic group Ar is selected from phenyl, 1-naphthyl, 2-naphthyl, 2-biphenyl, 4-biphenyl, (9H)-fluorenyl, phenanthryl, 9,10-dihydroanthryl or anthryl and the heterocyclic aromatic group is selected from 2- or 4-pyridyl, 2-, or 4-pyridinium, 2-pyrimidyl, 4-pyrimidinyl, 2-imidazolyl, 4-imidazolyl, 1,3,4-triazolyl, indolyl, quinolyl, isoquinolyl, benzthiazolyl, benzoxalyl, coumaryl, carbolinyl, phenanthrolinyl and carbazolyl.

More preferred, the invention relates to fluorescent or chromogenic carbapenems of formula I, characterized in that the carbocyclic aromatic group Ar is phenyl, 2-biphenyl or 4-biphenyl and the heterocyclic aromatic group Ar is 2-pyridyl, 4-pyridyl or 2-pyrimidinyl.

More preferred, the invention relates to fluorescent or chromogenic carbapenems of formula I, characterized in that the aromatic group Ar is carbocyclic and selected from phenyl, 2-biphenyl or 4-biphenyl.

More preferred, the invention relates to fluorescent or chromogenic carbapenems of formula I, characterized in that the aromatic group Ar is phenyl, 2-biphenyl or 4-biphenyl, $R_2$ is hydrogen and $R_3$ is acyl with 1 to 6 carbon atoms.

The β-lactams represent the most important and safest class of antibiotics. However, since the application of the penicillins resistance has become frequent and with gradually rising potency after extensive use of β-lactam antibiotics. Resistance is mainly caused by enzymes called β-lactamases. These bacterial enzymes catalyze the hydrolysis of the β-lactam moiety with the formation of inactive metabolites (Chemother. J. 2004, 13, 206). In 2001, more than 340 different betalactamases were known (Clin. Infect. Dis. 2001, 32, 1085).

Most recently, β-lactamases have become known, even capable of hydrolyzing carbapenems, which for a long time were regarded to be β-lactamase stable (JAMA, 2009, 301 (19), 1979). Although there are many classes of resistance enzymes, most of them can be classified as metallo-β-lactamases or serine-β-lactamases. They are abundant in many gram-negative bacteria e.g. in *Pseudomonas aeruginosa, Klebsiella pneumoniae, Escherichia coli, Proteus, Citrobacter* and others.

The detection of β-lactamases is most significant for hospital microbiologists to support their decision or advice how to treat bacterial infectious diseases. Moreover, by the early detection a misuse of antibiotics which can lead to further resistance and possibly to cross-infections in the hospitals can be minimized.

Chromogenic cephalosporins such as Nitrocefin, Padac or Centa (Journ. Amer. Chem. Soc. 1978, 100, 6491; Journ. Lab. Med. 1983, 7 (2), 33; Journ. Clin. Microbiol. 1982, 15 (5), 954) have been used as valuable tools for detection of β-lactamases. The chromogenic cephalosporins are excellent substrates for β-lactamase which catalyze the hydrolysis of their inherent β-lactam ring, which results in a change of colour. These widely used diagnostics are hydrolyzed virtually by all common β-lactamases including carbapenemases. Therefore, an easy differentiation between penicillinases, cephalosporinases or ESBLs versus carbapenemases, most important for determination of therapy, is not possible on this basis.

A fluorescent penicillin has become available for the detection of penicillin binding proteins (Antimicrob. Agents Chemother. 1999, 43 (5), 1124). A fluorescein-meropenem has been prepared for labelling of β-lactamases and was useful for detecting acyl-enzyme intermediates that form stable inhibitory complexes with carbapenems (Poster 23, Midwest Enzyme Chemistry Conference, University of Chicago, Oct. 4, 2008).

A non-β-lactam containing fluorescence marker carrying a mercapto group has been developed specifically to detect purified metallo-ezymes (Org. Biomol. Chem. 2003, 1, 17).

Fluorescence markers have also been developed for the detection of the DNS coding for β-lactamases.

Currently, there are three methods of detecting carbapenemases.

Microbiological Methods:

These tests are based on the determination of reduced bacterial susceptibility towards carbapenems, usually imipenem, meropenem or ertapenem. This can be done with agar diffusion tests. The antibiotics can be added with paper discs or can be dissolved in the agar, thus generating a selective medium for growth of only resistant strains. More reliably, bacterial resistance can be detected by minimum inhibitory concentration (MIC) determination. A currently used and recommended modification to investigate carbapenemase of *Klebsiella pneumoniae* is the modified Hodge test (clover leaf test), a technique using meropenem, the investigational bacterium and a different test bacterium *E. coli*. A specific test for metallo-β-lactamase is recommended by using ethylenediaminetetracetate (EDTA) and imipenem (Indian J. Med. Res. 2005, 121, 780).

The microbiological agar diffusion methods offer a rapid indication of resistance. The MIC determination is more laborious. On the other hand, susceptibility results depend largely on the inoculum and can lead to false results (clover leaf test, see Journ. Antimicrob. Chemother. 2010, 65 (2), 249). Moreover, the mixing of two different bacteria in the latter test, one highly resistant, the other susceptible, give rise to hazardous transfers of resistance genes. With microbiological methods alone, reduced susceptibility cannot unequivocally attributed to the occurrence of β-lactamases. Other mechanisms, e.g. decreased membrane permeability or alteration of the efflux system can also lead to reduced susceptibility to carbapenems (Science 1992, 257, 1064; Journ. Antimicrob. Chemother. 2005, 55 (6), 954; Ann. Clin. Lab. Sci. 2010, 40, 43).

Moreover, the microbiological method is not reliable for the detection of β-lactamase when mixtures of two or more different bacterial strains are investigated. Such mixed bacterial populations are frequent with samples of pathological bacteria.

Investigation of Enzymatic Activity:

β-lactamases of gramnegative bacteria can be solubilized by chemically or mechanically induced softening or lysis of the bacterial cell wall. The solubilized enzymes can be detected by their ability to deactivate imipenem in aqueous buffer solutions. During this reaction the UV spectrum of the substrate changes. This method is reliable for the detection of carbapenemases and their differentiation from cephalosporinases including extended spectrum β-lactamases (ESBL). However, the method requires additional equipment (UV spectrophotometer) and usually a purification of the enzymes in order to remove other UV-active compounds (Antimicrob. Agents and Chemother. 1996, 40 (9), 2080) and is hardly useful for routine investigations in a clinical laboratory.

Carbapenemase Gene Detection by Polymerase Chain Reaction (PCR):

This method is useful in rapid identification of β-lactamases including carbapenemases of one suspected type of bacterium, e.g. *Klebsiella pneumoniae* (www.hain-life-science.de: Check KPC-ESBL Systeme). The success of this method largely depends on the choice of a suitable primer. In 2001, more than 340 different betalactamases were known (Clin. Infect. Dis. 2001, 32, 1085). Consequently, because of the great variability of the numerous enzymes and bacteria, this technology is expending (BMJ 2008, 336 (7650); 927-30). For a general detection of all types of carbapenemases it is hardly useful in routine investigation. Moreover the method does not allow to differentiate between DNA from viable or dead bacteria (www.pflegewiki.de/wiki/Methicillinresistenter_*Staphylococcus_aureus*).

Therefore it was desirable to develop a general and reliable method for rapid and selective detection of all types of carbapenemases, allowing the medicinal staff an early decision whether a therapy with carbapenems is appropriate. The test should also allow to distinguish between less virulent ESBL (extended spectrum β-lactamase) and deadly carbapenemase. The test should be carried out within 24 hrs and be useful in routine investigations and in automated systems. The test should also be applicable for samples of mixed bacterial species.

Thus, the technical problem underlying the present invention is the provision of compounds suitable for the specific detection of bacterial carbapenemases.

The solution to this technical problem is achieved by the present invention:

In this patent application the first synthesis of a novel class of fluorescent carbapenems and their application as substrates for bacterial carbapenemase is described. The fluorescent property arises from an extension of the conjugated pi-system of the carbapenem-carboxylate moiety, inherent in all common carbapenem antibiotics (e. g. in meropenem) by incorporation of carbocyclic aromatic rings Ar, substituted with at least one electron withdrawing group. Alternatively, heterocyclic rings, that are electron withdrawing per se, can be incorporated. Only upon hydrolysis of the β-lactam ring the extended conjugation is broken and the fluorescence disappears. This is in contrast to the aforementioned fluorescein-meropenem label, wherein the fluorescein is attached to the side chain amine of meropenem and therefore lacking the required extended conjugation. In the latter case the fluorescence is essentially due to the label. It is expected to be retained after hydrolytic β-lactam cleavage.

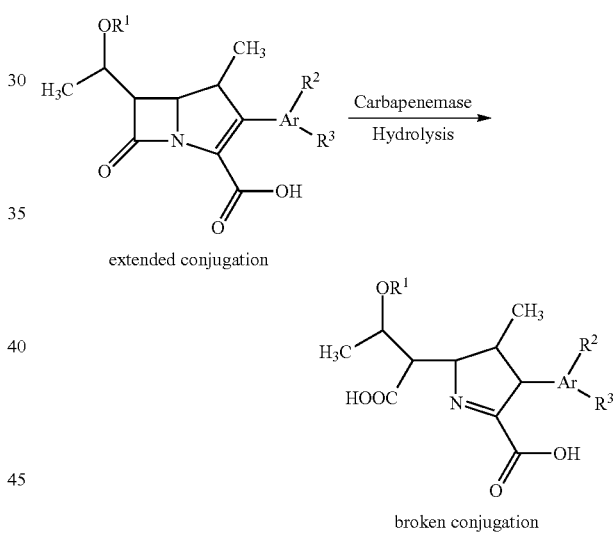

Consequently, in the present invention the presence of carbapenemase is proven by the rapid enzymatic hydrolysis and disappearance of the fluorescence. For the detection a standard laboratory (long wavelength) UV lamp of 366 nm is useful. Different from prior art chromogenic cephalosporins, e.g. nitrocefin, the novel fluorescent carbapenems are substrates strictly for carbapenemases, allowing the their differentiation from penicillinases, cephalosporinases and ESBL β-lactamases. By a slight modification of the test, simply by adding a specific inhibitor (EDTA) the enzymatic hydrolysis by metallo-β-lactamase can be prevented. Thus, after detection of a carbapenemase activity the bacterial enzymes can additionally be investigated in presence of EDTA and then coordinated to metallo-β-lactamases or other carbapenemases.

Surprisingly, the fluorescent carbapenems according to the invention displayed very large Stokes shifts of approximately 200 nm. In comparison, Green Fluorescent Protein (GPF) shows a Stokes shift of 114 nm.

The fluorescent carbapenems according to the invention are useful compounds to detect carbapenemases abundant in pathogenic bacteria, e.g. in *Pseudomonas aeruginosa*, *Klebsiella pneumoniae*, *Klebsiella oxytoca*, *Escherichia coli*, *Serratia marescens*, *Acinetobacter*, *Proteus* species, *Citrobacter* species, *Haemophilus influenza*, *Enterobacter cloacae*, *Enterobacter aerogenes*, *Moraxella catarrhalis*, *Acinetobacter baumannii*, *Aeromonas* species, *Salmonella* species and the like.

The fluorescent carbapenems according to the invention can also be used for the differentiation between carbapenem resistant gramnegative bacteria and carbapenem resistant grampositive bacteria, e. g. methicillin resistant *Staphylococcus aureus* or *enterococci*. The latter two bacterial species, although resistant to carbapenems, presently do not produce carbapenemase.

The fluorescent carbapenems according to the invention are universally useful for investigation and/or detection of carbapenemase in single bacterial strains or in bacterial mixtures also allowing the presence of mycobacteria or funghi. They are useful to investigate and/or detect carbapenemase in depressed strains of bacteria and strains with and without inducible carbapenemase. They allow to investigate and/or detect carbapenemase in the presence of other β-lactamases, e. g. penicillinases, cephalosporinases or ESBLs.

The fluorescent carbapenems according to the invention are also useful compounds for the rapid investigation and/or detection of known or suspected carbapenemase-inhibitors, for example serine protease inhibitors or metallo protease inhibitors or the like.

A process characterized in that a fluorescent carbapenem is hydrolyzed by a known or suspected carbapenemase allows to assess the presence and reactivity of the bacterial enzymes.

Certain bacteria produce substantial amounts of carbapenemase only upon growth in the presence of carbapenems, e. g. imipenem or cefoxitin, the latter acting as promoters. Such types of carbapenemases are known as inducible carbapenemases (Chemother. J. 2003, 12, 151-167). A relevant enzyme in the induction process is, e.g. glycoside hydrolase. The compounds according to the invention can also be useful for the investigation and/or detection of known or suspected inhibitors of carbapenemase inducing enzymes, e. g. glycoside hydrolase and the like. The inhibitor compounds can be β-lactam derived compounds or other small molecules (J. Biol. Chem. 2007, 282, 21382). In the presence of such inhibitors the induction of carbapenemase is no longer possible or substantially diminished. The compounds according to the invention are useful to evaluate such inhibitors e. g. by comparison of the amounts of induced carbapenemase after bacterial growth with and without inhibitor The above mentioned investigation and/or detection of inhibitors of carbapenemase inducing enzymes can be carried out with or without added promoters such as imipenem or cefoxitin. In the latter case, without added promoter, the compounds according to the invention can also adopt the role of promoter themselves.

The fluorescent carbapenems according to the invention are also useful compounds for the use in test kits.

The present invention relates to a kit for investigating and/or detecting microbial carbapenem resistance, comprising a compound as defined in the present invention, a ionic or non ionic detergent and a pharmaceutical carrier or diluent therefore, and instructions for use, in one ore more containers.

The carbapenemase inhibitor may be a serine protease inhibitor or a metallo protease inhibitor or the like.

For rational application of the compounds according to the invention can be mixed with other components, also necessary for detecting carbapenem resistance. Such components are, e. g. solid buffer compounds, solid nutrition media, solid salts, solid antibiotics and/or solid ionic or non ionic detergents. The resulting compositions can be stored in dry state over a long period of time and dissolved immediately before investigation and/or detection of carbapenem resistance. A preferred solvent for dissolution is water or aqueous sodium chloride solution. Especially preferred is sterile water or sterile sodium chloride solution.

The fluorescent carbapenems according to the invention can be used to detect β-lactamases in a diluent, preferably water, most preferably in aqueous buffer solutions at a pH range of 4 to 9, a preferred range is 5 to 8, strongly preferred is pH 7.4. The character of the buffer is variable. Examples of such media are phosphate, tris- or HEPES buffers. Preferred buffers are based on phosphate or hydrogen carbonate. The diluents can be used as such or supplemented with organic solvents, e.g. ethanol, isopropanol and dimethyl sulfoxide or with salts, e.g. sodium chloride or potassium chloride or with compounds which allow permeabilisation or lysis of the bacterial cell walls. Such compounds or mixtures of compounds are known in the art and/or are commercially available. Examples of such additives are polymyxin B, neomycin, tris-hydrochloride and the like (Antimicrob. Agents Chemotherapy 1984, 26 (1), 48) or ionic or non ionic detergents, e.g. SDS, sodium cholate or deoxycholate, alkylphosphine oxide detergents, e.g. dimethyldecyiphosphine oxide, N,N-bis-β-gluconamidopropyl) cholamide (CHAP), polyoxyethylenglycol ethers, e.g. polyoxyethylenglycol dodecylether, octaethylenglycol mono-n-dodecylether, polyoxyethylene (23) lauryl ether or glucosides of fatty alcohols, e.g dodecylglucopyranoside and the like. In addition to the bacterial components and the fluorescent carbapenem the test medium may also contain a variety of other ingredients such as inorganic salts, e. g. zinc or iron salts and/or growth inhibitors, e. g. sodium sulfite or antibiotics, e. g. chlorohexidine, azthreonam, quinolones or polymyxin B and the like.

When carried out in aqueous buffer solution a prerequisite for the success of the inventive enzymatic test reaction is that the cytoplasmatic carbapenemase is accessible by the fluorescent carbapenem. In many cases this requires a pretreatment of the cell wall of the bacterial species. Besides the aforementioned chemical methods, other procedures, known in the art, e.g. mechanical work up by the French press or by ultrasonic treatment, treatment with hypotonic or hypertonic aqueous salt solutions or repeated freezing and thawing of the bacteria are useful for sample preparations. The corresponding technology is known in the art per se.

The range of temperature in the enzymatic hydrolysis process using buffer solution is 15° C. to 50° C., the preferred range of temperature is 20° C. to 40° C. Strongly preferred are room temperature or 37° C.

The disappearance of the fluorescence after enzymatic hydrolysis can be detected simply by vision in UV light. In automated systems it is preferred to monitor the emitted fluorescence light by electronic devices, e.g. photo cells or photo transistors and the like, allowing to investigate the enzymatic hydrolysis continuously by quantitative determination of the fluorescence of the remaining compounds according to the invention. The comparison of the initial fluorescence with that of a relatively early stage of the enzymatic hydrolysis reaction allows to establish the presence of carbapenemases within a shorter period of time.

It was found, that the individual types of carbapenemases hydrolyze the fluorescent carbapenems at different rates, from minutes to a few hours. The rates of hydrolyses parallel those observed with the antibiotics meropenem or imipenem. Consequently the fluorescent carbapenems do not only allow to detect the presence of the present bacterial enzyme, but also allow a further investigation: By such investigation the reactivity of the present bacterial enzyme can be determined, allowing the therapist to assess the severity of the infectious disease.

Alternatively, the enzymatic test reaction using the fluorescent carbapenems can be performed with native bacteria in a nutrition medium, e.g. Müller-Hinton broth. In such media the bacterial inoculum is incubated together with the fluorescent carbapenem according to the invention. During exponential growth of the bacteria large amounts of carbapenemase is produced allowing complete hydrolysis of the fluorescent carbapenems with concomitant extinction of the yellow fluorescence.

The temperature using nutrition media is 30 to 40° C. The preferred temperature settings are 32° C. or 37° C. Strongly preferred is 37° C.

To assess the presence of metallo-β-lactamase, in addition to the fluorescent carbapenem and the aforementioned supplements, the test medium may contain specific inhibitors of metallo-β-lactamases, e.g. complexing agents such as ethylenetetramine acetic acid. After addition of such inhibitors the abundant metallo-β-lactamase (but nor other carbapenemases) can be deactivated. The hydrolysis of the fluorescent carbapenem is then no longer possible by metallo-R-lactamases. By performing parallel experiments, i. e. with and without inhibition of the enzymatic test reaction a differentiation between metallo- or non-metallo carbapenemases becomes possible. Alternatively, the metallo-β-lactamase can be characterized by addition of zinc salts, e. g. zinc sulphate to the test medium, able to accelerate the hydrolysis by these specific enzymes.

The salts of the compounds of formula I are inorganic or organic salts, for example lithium, sodium, potassium or magnesium, calcium or zinc salts. Organic salts are salts derived from organic bases, for example procaine, trialkyammonium, amidinium or guanidinium salts. The salts can occur as lyophilized powders or can exist in the crystalline state. Preferred salts are well soluble in aqueous solution, e.g. magnesium, potassium or sodium salts. Strongly preferred are sodium or potassium salts.

Alternatively, the salts can exist as inner or zwitterionic salts. Such inner salts can arise from the incorporation of basic groups $R^2$ or $R^3$, e. g. amino, lower monoalyklamino or dialkylamino groups or amidino or guanidine groups. Moreover, inner salts can also arise from the basicity of the aromatic group Ar itself, e. g. Ar=imidazolyl or 1,3,4-triazolyl.

In formula I carbocyclic aromatic groups Ar are derived from aromatic hydrocarbons. Examples of such groups are phenyl, 1- or 2-naphthyl, 4-biphenyl, (9H-fluorenyl), phenanthryl, anthryl or 9,10-dihydroanthryl groups. Preferred carbocyclic groups are phenyl or biphenyl. Strongly preferred is phenyl. The electron withdrawing substituents $R^2$ and $R^3$ are preferably attached in the ortho and/or para position of the phenyl groups Ar relative to the position of the attached carbapenem nucleus. With mono substitution ($R^2$=H) the para position of the substituent is strongly preferred.

With 1-naphthyl groups the electron withdrawing substituents are preferably attached at the 2, 4 or 5-positions to allow the extended conjugation of the pi-electron system.

As for disubstituted 1,1'-biphenyl groups Ar the electron withdrawing substituents $R^2$ and $R^3$ are preferably attached in the 3, 2', or 4'-position and the carbapenem nucleus is attached in the 4-position. For monosubstituted 1,1'-biphenyl groups ($R^2$=H) the electron withdrawing group $R^3$ is preferably attached in the 3 or 4'-position and the carbapenem nucleus is attached in the 4-position.

9H-fluorenyl groups Ar are preferably connected to the carbapenem nucleus in their 3-position, the electron withdrawing oxo substituent is attached at the 9-position allowing to extend the conjugation.

In formula I the heterocyclic aromatic groups Ar are derived from aromatic heterocycles. Examples of such monocyclic groups are 2- or 4-pyridyl, 2, or 4-pyridinium, 2-pyrimidyl, 4-pyrimidinyl, 2-imidazolyl, 4-imidazolyl and 1,3,4-triazolyl. Preferred is 4-pyridyl. 2 and 4 positions of the (optional) substituents $R^2$ and $R^3$ are preferred.

Examples of bicyclic heterocyclic aromatic groups Ar are indolyl, quinolyl, isoquinolyl, benzthiazolyl, benzoxalyl, coumaryl and the like.

Examples of tricyclic heterocyclic groups Ar are carbolinyl, phenanthrolinyl, carbazolyl and the like.

With the compounds having carbocyclic groups Ar for a substantial change of colour or fluorescence during enzymatic hydrolysis by carbapenemase, it is essential that at least one electron withdrawing substituent (e.g. $R^3$) is attached in suitable positions to allow the extension of the conjugated pi-system. With phenyl groups Ar, these are the o,p-positions. For the same reason, in electron deficient heterocyclyl groups Ar, the hetero atoms must preferably be located in the o,p-positions.

A prerequisite for chromgenic or fluorescent feature is the electron withdrawing nature of the attached aromatic group Ar. The electron withdrawing effect can arise, for example with carbocyclic Ar groups, from the attached substituents $R^2$ and $R^3$. For a maximum electron withdrawing effect $R^2$ and $R^2$ are both electron withdrawing substituents, e. g. both are acetyl groups. However, as shown in the Example Section, fluorescence is already achieved with one electron withdrawing substituent, e. g. with Ar=phenyl, $R^2$=H, $R^3$=acetyl). Therefore the nature of the second (non electron withdrawing) substituent is not very critical. Such substituents may even be electron donating groups, e.g. amino or hydroxy and the like. The aim of using such substituents is, for example, to increase solubility in aqueous solution.

As for compounds according to the invention with heterocyclic groups Ar the above mentioned electron withdrawing character can already be achieved without additional electron withdrawing substituents $R^2$ and $R^3$, e. g. in Ar=2- or 4-pyridyl. The presence and the electron withdrawing effect of such substituents are again not critical, as long the heterocyclic aromatic part Ar is sufficiently electron withdrawing.

2-Arylcarbapenems, groups have been prepared and assayed for antibiotic activity according to J. Med. Chem. 1987, 30, 871-880. However, they lacked one or two additional electron withdrawing groups. In our hands, simple 2-phenylcarbapenems did not show any colour or fluorescence and therefore were not useful for simple detection of carbapenemase according to the invention. Similarly, in reported 3-pyridylcarbapenems the electron withdrawing effect is not large enough to allow the formation of colour or fluorescence and therefore this quality neither was observed nor reported.

1-Unsubstituted-2-(9-oxo-(9H)-fluoren-2-yl)carbapenems were also assayed for antibiotic activity reported in EP 472306. However, in these compounds the electron withdrawing oxo group is in the wrong (meta) position. Again colour or fluorescence was not reported. A substantial change in fluorescence colour during enzymatic hydrolysis cannot be expected.

The compounds of formula I and their salts can exist in several stereoisomeric forms. Preferred forms are those with the (5R) configuration according to the bicyclo nomenclature. Strongly preferred are the compounds having the (4S,5R,6S) configuration, i. e. a geometry analogous to that of conventional carbapenem antibiotics. The preferred configuration of the 6-hydroxyethyl group or its alkylated or acylated forms is 1'R.

The fluorescent carbapenems according to the invention are prepared according to the following reaction scheme:

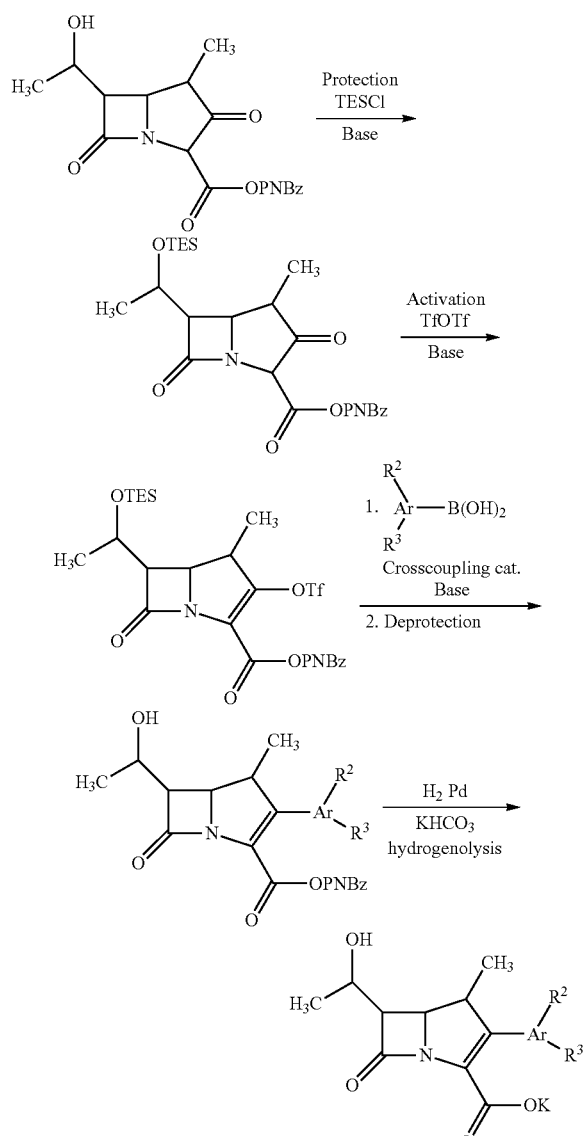

The synthesis of the TES protected keto ester is described in J. Organomet. Chem. 2002, 253, 279-287.

The protection of the alcoholic group can be carried out by using protecting groups which are known per se. Such groups are described, e. g. in T. W. Greene and P. G. M. Wuts, "Protective Groups in Organic Synthesis", Wiley, New York, p. 10-118. Preferred protection groups are groups that are easily removed by mild acid treatment, e. g. triakylsilyl groups or by hydrogenolysis, e. g. p-nitrobenzyloxycarbonyl groups or by rhodium catalysts, e.g. allyloxycarbonyl groups.

As for the ester groups which also function as protecting groups of the carboxylic acid moiety, a great variability can be used and is known per se and published in the above mentioned reference on pages 224-276. Very suitable protecting groups, especially useful for β-lactam chemistry are reported in H. Wild "The Organic Chemistry of β-Lactams (I. Georg Ed.) VCH New York 1992, p. 1-48. Preferred protecting groups of the carboxylic acid are allyl, acetonyl, p-methoxybenzyl, p-nitrobenzyl and the like. The deprotecting chemistry is known per se and also described in the above-mentioned references. Examples of deprotecting procedures are rhodium catalyzed cleavage, mild alkaline hydrolysis or hydrogenolysis and the like.

Alternatively, in the protection step triethyl silyl chloride (TESCI) can be replaced by an alkyl iodide, leading to the product of formula I ($R^1$=alkyl) or an acyl chloride, leading to I ($R^1$=acyl). Alternatively, these types of products can also be obtained by alkylation or acylation of the hydroxyl group after the cross coupling and deprotection step. The alkyl or acyl groups $R^1$ are retained during the hydrogenolysis, thus affording compounds of formula I with $R^1$=alkyl or acyl.

In the cross coupling step a variety of palladium catalysts can be used as described in Tet. Lett. 1993, 34, 3211-3214 or J. Organomet. Chem. 2002, 253, 279-287. A preferred crosscoupling catalyst is $Pd(dba)_2$. The reaction is carried out in an organic solvent, preferably tetrahydrofuran or methylene chloride, preferably at room temperature. As a base, an organic base, e.g. triethylamine or diisopropylethylamine or an inorganic base, e.g. sodium hydroxide or potassium phosphate are useful. Preferred are triethylamine or potassium phosphate.

The examples below illustrate the preparation and use of the compounds according to the invention:

EXAMPLE 1

Preparation of potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate

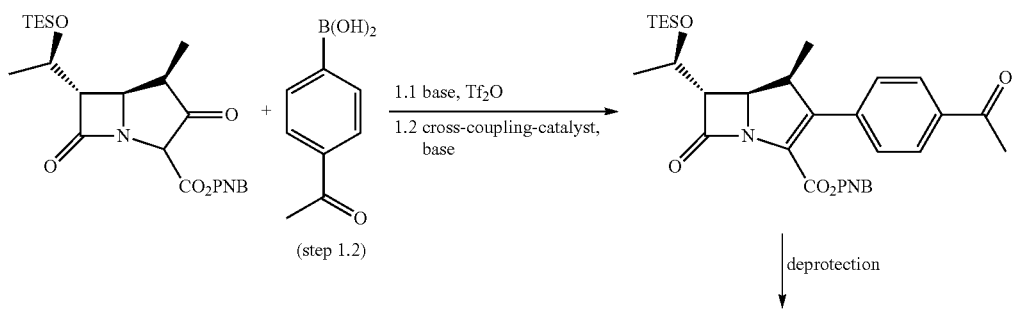

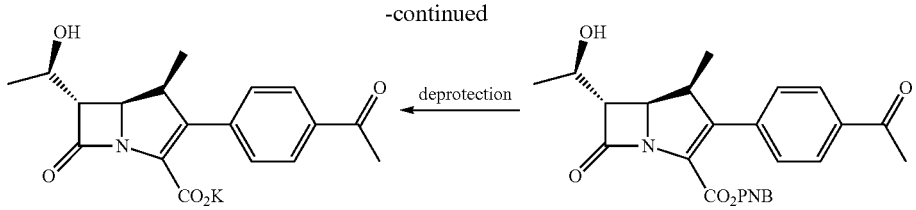

(4S,5R,6S)-3-(4-acetyl-phenyl)-4-methyl-7-oxo-6-((1'R)-triethylsilanyloxy-ethyl)-1-aza-bicyclo[3.2.0]hept-2-ene-2-carboxylic acid 4-nitro-benzyl-ester In a 25 ml Schlenk flask fitted with a rubber septum, magnetic stirrer and a balloon filled with dry nitrogen at −78° C. to a solution of (4R,5S,6S)-4-methyl-3,7-dioxo-6-((1'R)-triethylsilanyloxy-ethyl)-1-aza-bicyclo[3.2.0]heptane-2-carboxylic acid 4-nitro-benzyl-ester (526 mg, 1.10 mmol) in dry dichloromethane (4.3 ml) was added triethylamine (153 µl, 1.10 mmol). After 15 min, trifluoromethanesulfonic anhydride (187 µl, 1.10 mmol) was added to the resulting orange-yellow solution. After 30 min at −78° C., Pd(dba)$_2$ (33 mg, 0.057 mmol, 5 mol %), a solution of 4-acetyl-phenyl-boronic acid (158 mg, 0.96 mmol) in tetrahydrofuran (7.2 ml), and K$_3$PO$_4$ (712 mg, 3.35 mmol) were added sequentially. The dry-ice/acetone bath was removed and the mixture was allowed to warm to ambient temperature. Upon reaction completion, the wine-red solution was diluted in toluene (200 ml), washed three times with portions (50 ml) of water and once with brine (50 ml) and dried over magnesium sulfate. After filtration, the solvent was removed in a vacuum rotary evaporator, leaving a brownish oil. The crude product was purified by silica gel column chromatography using toluene-ethyl acetate (19:1) yielding a yellow oil (200 mg, 36%). IR-spectrum (ATR): 2956, 2876, 2359, 2344, 1779, 1730, 1684, 1605, 1523, 1457, 1431, 1403, 1376, 1346, 1264, 1228, 1190, 1148, 1108, 1015, 958, 847, 804, 736, 697 cm$^{-1}$.

(4S,5R,6S)-3-(4-acetyl-phenyl)-4-methyl-7-oxo-6-((1'R)-hydroxy-ethyl)-1-aza-bicyclo[3.2.0]hept-2-ene-2-carboxylic acid 4-nitro-benzyl-ester In a 50 ml round-bottom flask fitted with a rubber septum and a magnetic stirrer at room temperature to a solution of (4S,5R,6S)-3-(4-acetyl-phenyl)-4-methyl-7-oxo-6-((1'R)-triethylsilanyloxy-ethyl)-1-aza-bicyclo[3.2.0]hept-2-ene-2-carboxylic acid 4-nitro-benzyl-ester (190 mg, 0.328 mmol) in tetrahydrofuran (48 ml) and water (9.5 ml) was added aqueous hydrochloric acid (1.0 M, to pH 2.3). After stirring for 1 h, the yellow solution was diluted in dichloromethane (180 ml), washed once with 10% aqueous NaHCO$_3$ (60 ml), twice with portions (50 ml) of water and dried over magnesium sulfate. After filtration, the solvent was removed in a vacuum rotary evaporator. A yellow oil (195 mg) was obtained. IR-spectrum (ATR): 3444, 2957, 2875, 1773, 1725, 1682, 1601, 1521, 1456, 1432, 1403, 1378, 1346, 1265, 1195, 1107, 1014, 959, 911, 845, 774, 733, 696 cm$^{-1}$.

Potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate In a 25 ml Schlenk flask fitted with a magnetic stirrer, hydrogenation burette and a balloon filled with hydrogen at 0° C. to a suspension of palladium on activated carbon (25 mg, 10%) in tetrahydrofuran (1.8 ml) was added a solution of (4S,5R,6S)-4-methyl-3,7-dioxo-6-((1'R)-hydroxy-ethyl)-1-aza-bicyclo[3.2.0]heptane-2-carboxylic acid 4-nitro-benzyl-ester (50 mg, 0.11 mmol) in tetrahydrofuran (0.7 ml) and aqueous KHCO$_3$ (1.1 ml, 0.1 M). The reaction suspension was stirred under hydrogen atmosphere. After 20 min, the catalyst was centrifuged off and the supernatant liquid was decanted off. The black residue was washed once with a mixture (5 ml) of tetrahydrofuran and water (2:1). The combined aqueous layers were washed twice with portions (4 ml) of ethyl acetate and the aqueous layer was concentrated to small volume under vacuum. After sterile filtration and lyophilization at −25° C., a yellow foam (32 mg, 80%) was obtained. IR-spectrum (ATR): 3283, 2926, 2541, 1750, 1677, 1602, 1394, 1265, 1141, 1015, 838, 690 cm$^{-1}$.

EXAMPLE 2

Preparation of potassium-(4S,5R,6S)-6-[(1'R)-hydroxy-ethyl]-4-methyl-7-oxo-3-(4-amino-phenyl)-1-aza-bicyclo[3.2.0]hept-2-ene-2-carboxylate

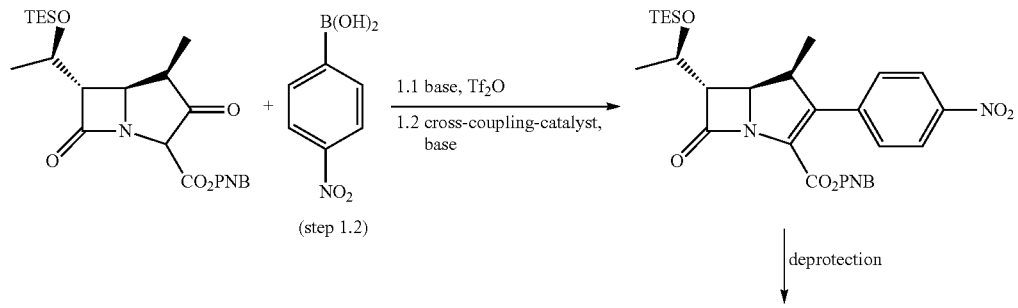

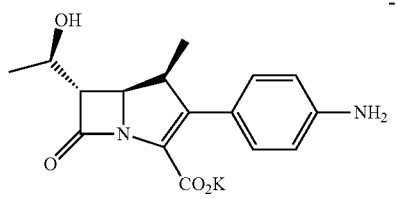 deprotection 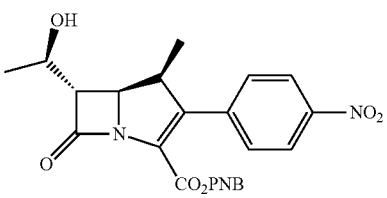

(4S,5R,6S)-4-methyl-3-(4-nitro-phenyl)-7-oxo-6-((1'R)-triethylsilanyloxy-ethyl)-1-aza-bicyclo[3.2.0]hept-2-ene-2-carboxylic acid 4-nitro-benzyl-ester In a 25 ml Schlenk flask fitted with a rubber septum, magnetic stirrer and a balloon filled with dry nitrogen at −78° C. to a solution of (4R,5S,6S)-4-methyl-3,7-dioxo-6-((1'R)-triethylsilanyloxy-ethyl)-1-aza-bicyclo[3.2.0]heptane-2-carboxylic acid 4-nitro-benzyl-ester (440 mg, 0.92 mmol) in dry dichloromethane (3.6 ml) was added triethylamine (128 µl, 0.92 mmol). After 15 min, trifluoromethanesulfonic anhydride (156 µl, 0.92 mmol) was added to the resulting orange-yellow solution. After 30 min at −78° C., Pd(dba)$_2$ (28 mg, 0.048 mmol, 5 mol %), a solution of 4-nitro-phenyl-boronic acid (132 mg, 0.80 mmol) in tetrahydrofuran (6.0 ml), and aqueous potassium hydroxide (520 µl, 2.28 mmol, 5.4 M) were added sequentially. The dry-ice/acetone bath was removed and the mixture was allowed to warm to ambient temperature. Upon reaction completion, the brown solution was diluted in toluene (200 ml), washed three times with portions (50 ml) of water and once with brine (50 ml) and dried over magnesium sulfate. After filtration, the solvent was removed in a vacuum rotary evaporator, leaving a brownish oil. The crude product was purified by silica gel column chromatography using toluene-ethyl acetate (19:1) yielding a yellow oil (100 mg, 21%). IR-spectrum (ATR): 3079, 2955, 2910, 2875, 1776, 1725, 1601, 1517, 1456, 1413, 1376, 1345, 1290, 1271, 1192, 1145, 1105, 1088, 1052, 1002, 962, 850, 805, 770, 736, 697, 616 cm$^{-1}$.

(4S,5R,6S)-6-((1'R)-Hydroxyethyl)-4-methyl-3-(4-nitro-phenyl)-7-oxo-1-aza-bicyclo[3.2.0]hept-2-ene-2-carboxylic acid 4-nitro-benzyl-ester In a 50 ml round-bottom flask fitted with a rubber septum and a magnetic stirrer at room temperature to a solution of (4S,5R,6S)-4-methyl-3-(4-nitro-phenyl)-7-oxo-6-((1'R)-triethylsilanyloxy-ethyl)-1-aza-bicyclo[3.2.0]hept-2-ene-2-carboxylic acid 4-nitro-benzyl-ester (100 mg, 0.17 mmol) in tetrahydrofuran (25 ml) and water (5 ml) was added aqueous hydrochloric acid (1.0 M, to pH 2.3). After stirring for 2 h, the yellow solution was diluted in dichloromethane (180 ml), washed three times with portions (60 ml) of water and dried over magnesium sulfate. After filtration, the solvent was removed in a vacuum rotary evaporator. A yellow oil was obtained, which was purified by silica gel column chromatography using toluene-ethyl acetate (2:1) yielding a yellow oil (60 mg, 75%). IR-spectrum (ATR): 3502, 3112, 3080, 2968, 2930, 2873, 2856, 1769, 1722, 1602, 1600, 1514, 1454, 1379, 1344, 1274, 1192, 1139, 1103, 1037, 1014, 936, 910, 850, 806, 772, 751, 731, 697, 648 cm$^{-1}$.

Potassium-(4S,5R,6S)-6-[(1'R)-hydroxy-ethyl]-4-methyl-7-oxo-3-(4-amino-phenyl)-1-aza-bicyclo[3.2.0]hept-2-ene-2-carboxylate In a 25 ml Schlenk flask fitted with a magnetic stirrer, hydrogenation burette and a balloon filled with hydrogen at 0° C. to a suspension of palladium on activated carbon (30 mg, 10%) in tetrahydrofuran (1.8 ml) was added a solution of (4S,5R,6S)-6-((1'R)-Hydroxyethyl)-4-methyl-3-(4-nitro-phenyl)-7-oxo-1-aza-bicyclo[3.2.0]hept-2-ene-2-carboxylic acid 4-nitro-benzyl-ester (30 mg, 0.064 mmol) in tetrahydrofuran (0.7 ml) and aqueous KHCO$_3$ (0.64 ml, 0.1 M). The reaction suspension was stirred under hydrogen atmosphere. After 10 min, the catalyst was centrifuged off and the supernatant liquid was decanted off. The black residue was washed once with a mixture (5 ml) of tetrahydrofuran and water (2:1). The combined aqueous layers were washed twice with portions (4 ml) of ethyl acetate and the aqueous layer was concentrated to small volume under vacuum. After sterile filtration and lyophilization at −25° C., a yellow foam (9 mg, 42%) was obtained. IR-spectrum (ATR): 3342, 2958, 1733, 1606, 1513, 1393, 1296, 1263, 1218, 1179, 1137, 841 cm$^{-1}$.

EXAMPLE 3

Preparation of potassium-(4S,5R,6S)-3-(4'-acetyl-biphenyl-4-yl)-6-[(1'R)-hydroxyethyl]-4-methyl-7-oxo-1-aza-bicyclo[3.2.0]hept-2-ene-2-carboxylate

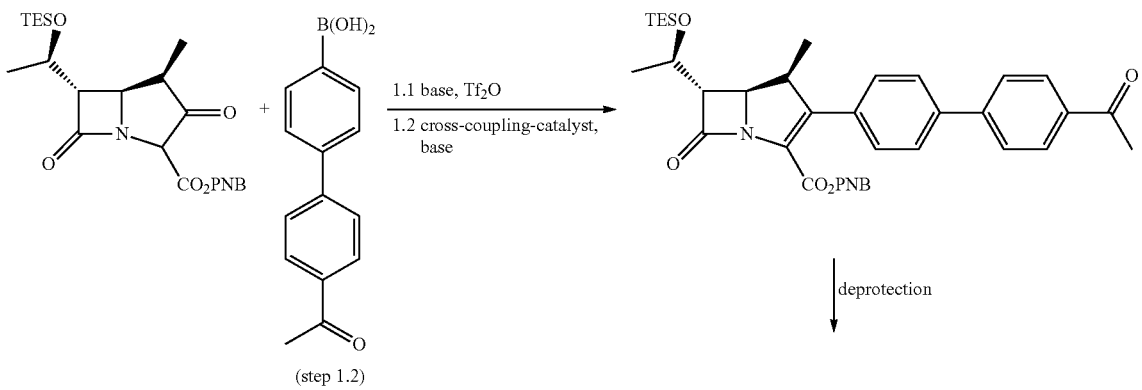

(step 1.2)

deprotection

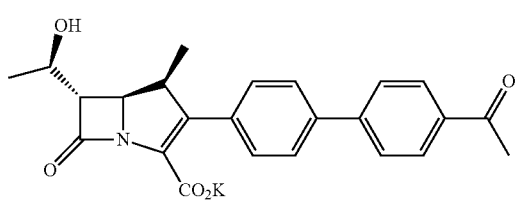 —continued 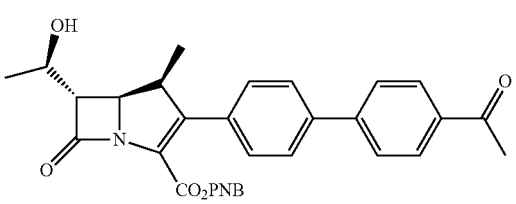

(4S,5R,6S)-3-(4'-Acetyl-biphenyl-4-yl)-4-methyl-7-oxo-6-((1'R)-triethylsilanyloxy-ethyl)-1-aza-bicyclo[3.2.0]hept-2-ene-2-carboxylic acid 4-nitro-benzyl-ester In a 25 ml Schlenk flask fitted with a rubber septum, magnetic stirrer and a balloon filled with dry nitrogen at −78° C. to a solution of (4R,5S,6S)-4-methyl-3,7-dioxo-6-((1'R)-triethylsilanyloxy-ethyl)-1-aza-bicyclo[3.2.0]heptane-2-carboxylic acid 4-nitro-benzyl-ester (110 mg, 0.23 mmol) in dry dichloromethane (0.9 ml) was added triethylamine (32 µl, 0.23 mmol). After 15 min, trifluoromethanesulfonic anhydride (39 µl, 0.23 mmol) was added to the resulting orange-yellow solution. After 30 min at −78° C., $Pd(dba)_2$ (7 mg, 0.012 mmol, 5 mol %), a solution of 4'-acetyl-biphenyl boronic acid (48 mg, 0.20 mmol) in tetrahydrofuran (2.5 ml), and aqueous potassium hydroxide (130 µl, 0.7 mmol, 5.4 M) were added sequentially. The dry-ice/acetone bath was removed and the mixture was allowed to warm to ambient temperature. Upon reaction completion, the wine-red solution was diluted in toluene (170 ml), washed three times with portions (40 ml) of water and once with brine (40 ml) and dried over magnesium sulfate. After filtration, the solvent was removed in a vacuum rotary evaporator, leaving a brownish oil. The crude product was purified by silica gel column chromatography using toluene-ethyl acetate (19:1) yielding a yellow oil (23 mg, 18%). IR-spectrum (ATR): 2957, 2876, 1773, 1724, 1681, 1603, 1521, 1496, 1457, 1415, 1376, 1346, 1264, 1228, 1190, 1148, 1053, 1004, 958, 818, 736 cm$^{-1}$.

(4S,5R,6S)-3-(4'-Acetyl-biphenyl-4-yl)-6-((1'R)-hydroxy-ethyl)-4-methyl-7-oxo-1-aza-bicyclo[3.2.0]hept-2-ene-2-carboxylic acid 4-nitro-benzyl-ester In a 50 ml round-bottom flask fitted with a rubber septum and a magnetic stirrer at room temperature to a solution of (4S,5R,6S)-3-(4'-Acetyl-biphenyl-4-yl)-4-methyl-7-oxo-6-((1'R)-triethylsilanyloxy-ethyl)-1-aza-bicyclo[3.2.0]hept-2-ene-2-carboxylic acid 4-nitro-benzyl-ester (20 mg, 0.031 mmol) in tetrahydrofuran (5 ml) and water (1 ml) was added aqueous hydrochloric acid (1.0 M, to pH 2.3). After stirring for 40 min, the yellow solution was diluted in dichloromethane (180 ml), washed once with 10% aqueous NaHCO$_3$ (60 ml), twice with portions (50 ml) of water and dried over magnesium sulfate. After filtration, the solvent was removed in a vacuum rotary evaporator. A yellow oil was obtained (23 mg). IR-spectrum (ATR): 3438, 2957, 2925, 2855, 1770, 1724, 1679, 1604, 1521, 1496, 1456, 1377, 1346, 1266, 1187, 1140, 1106, 1039, 1016, 1004, 959, 909, 819, 768, 731, 648 cm$^{-1}$.

Potassium-(4S,5R,6S)-3-(4'-acetyl-biphenyl-4-yl)-6-[(1'R)-hydroxyethyl]-4-methyl-7-oxo-1-aza-bicyclo[3.2.0]hept-2-ene-2-carboxylate In a 25 ml Schlenk flask fitted with a magnetic stirrer, hydrogenation burette and a balloon filled with hydrogen at 0° C. to a suspension of palladium on activated carbon (9 mg, 10%) in tetrahydrofuran (1.8 ml) was added a solution of (4S,5R,6S)-3-(4'-Acetyl-biphenyl-4-yl)-6-((1'R)-hydroxy-ethyl)-4-methyl-7-oxo-1-aza-bicyclo[3.2.0]hept-2-ene-2-carboxylic acid 4-nitro-benzyl-ester (17 mg, 0.031 mmol) in tetrahydrofuran (0.7 ml) and aqueous KHCO$_3$ (0.31 ml, 0.1 M). The reaction suspension was stirred under hydrogen atmosphere. After 10 min, the catalyst was centrifuged off and the supernatant liquid was decanted off. The black residue was washed once with a mixture (5 ml) of tetrahydrofuran and water (2:1). The combined aqueous layers were washed twice with portions (4 ml) of ethyl acetate and the aqueous layer was concentrated to small volume under vacuum. After sterile filtration and lyophilization at −25° C., a yellow foam (4.4 mg, 59%) was obtained. IR-spectrum (ATR): 3364, 2925, 2727, 1743, 1674, 1631, 1602, 1400, 1267, 1112, 1007, 830, 704 cm$^{-1}$.

EXAMPLE 4

Preparation of potassium-(4S,5R,6S)-3-(4-acetyl-phenyl)-6-[(1'R)-acetoxyethyl]-4-methyl-7-oxo-1-aza-bicyclo[3.2.0]hept-2-ene-2-carboxylate

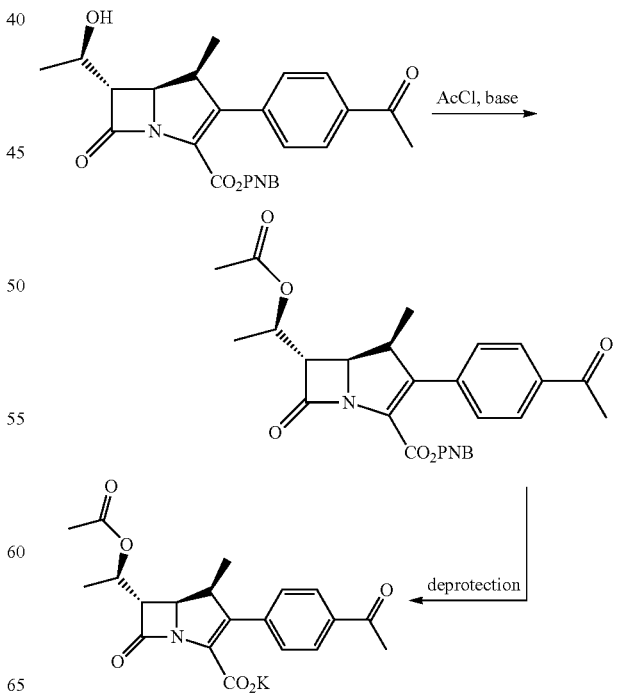

(4S,5R,6S)-3-(4'-Acetyl-biphenyl-4-yl)-6-((1'R)-acetoxy-ethyl)-4-methyl-7-oxo-1-aza-bicyclo[3.2.0]hept-2-ene-2-carboxylic acid 4-nitro-benzyl-ester In a 10 ml Schlenk flask fitted with a rubber septum, magnetic stirrer and a balloon filled with dry nitrogen at 0° C. to a solution of (4S,5R,6S)-4-methyl-3,7-dioxo-6-((1'R)-hydroxy-ethyl)-1-aza-bicyclo[3.2.0]heptane-2-carboxylic acid 4-nitro-benzyl-ester (10 mg, 0.022 mmol) in dry dichloromethane (2.0 ml) was added a solution of dimethylpyridin-4-yl-amine (2.7 mg, 0.022 mmol) in dry dichloromethane (0.5 ml). Acetic acid chloride (1.6 µl, 0.022 mmol) was added. After 1 h at 0° C., the opaque solution was diluted in toluene (20 ml), washed once with saturated aqueous $NaHCO_3$ (10 ml), once with water (10 ml), once with brine (10 ml) and dried over magnesium sulfate. After filtration, the solvent was removed in a vacuum rotary evaporator. A yellow oil was obtained (10 mg). IR-spectrum (ATR): 3420, 2960, 2927, 2874, 1777, 1728, 1682, 1646, 1601, 1562, 1521, 1455, 1374, 1346, 1264, 1237, 1192, 1107, 1073, 1015, 957, 912, 847, 807, 775, 734, 696 $cm^{-1}$.

Potassium-(4S,5R,6S)-3-(4-acetyl-phenyl)-6-[(1'R)-acetoxyethyl]-4-methyl-7-oxo-1-aza-bicyclo[3.2.0]hept-2-ene-2-carboxylate was prepared according to example 1.

EXAMPLE 5

Detection of *Klebsiella pneumoniae* carbapenemases (KPC) by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate after physical disruption by sonication Bacterial strain *Klebsiella pneumoniae* (producing KPC-2, Heidelberg) was grown over night at 37° C. (220 rpm) in Mueller-Hinton-Broth (10 ml) using a 45-ml-Falcon tube, harvested by centrifugation at 13.000 rpm (2 min, 1 ml for analytical studies, McFarland 10), washed once with PBS (1 ml), and resuspended in PBS (500 µl). Subsequently the cells were lysed by sonication with a Bandelin Sonopuls (5×15 s), pulsed at 80% max. power. Further PBS (500 µl) and fluorogenic carbapenem (100 µg) were added. After storage at room temperature for 5 min, the disappearance of the green-yellow fluorescence colour (UV light λ=366 nm) could be observed, indicating the production of carbapenemases by *Klebsiella pneumoniae*.

EXAMPLE 6

Detection of *Klebsiella pneumoniae* carbapenemases (KPC) by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate during physical disruption by sonication with glass beads Bacterial strain *Klebsiella pneumoniae* (producing KPC-2, Heidelberg) was grown over night at 37° C. in Mueller-Hinton-Broth (10 ml). To a sample (1 ml, McFarland 0.5) were added fluorogenic carbapenem (100 µg) and glass beads (100 mg, Sigma-Aldrich, G9018, 150-212 µm, unwashed) using a 5-ml-glass-tube with a plane bottom. The cells were lysed by sonication with a commercial available ultrasound bath. After treatment for 45 min, the disappearance of the green-yellow fluorescence colour (λ=366 nm) could be observed, indicating the production of carbapenemases by *Klebsiella pneumoniae*.

EXAMPLE 7

Detection of inducible (Oxa-type) carbapenemases of *Escherichia coli* by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate after physical disruption by sonication Bacterial strain *Escherichia cog* (producing Oxa-48, Heidelberg) was grown over night at 37° C. (220 rpm) in Mueller-Hinton-Broth (10 ml) using a 45-ml-Falcon tube. A sample (1 ml, McFarland 10) was diluted in Mueller-Hinton-Broth (10 ml) and incubated with Imipenem (2 µg/ml) for 4 h using a 45-ml-Falcon tube. After centrifugation at 13.000 rpm (2 min, 1 ml for analytical studies), the sample was washed once with PBS (1 ml) and resuspended in PBS (500 µl). Subsequently the cells were lysed by sonication with a Bandelin Sonopuls (5×15 s), pulsed at 80% max. power. Further PBS (500 µl) and fluorogenic carbapenem (100 µg) were added. After storage at room temperature for 5 min, the disappearance of the green-yellow fluorescence colour (UV light λ=366 nm) could be observed, indicating the production of Oxa-48-carbapenemases by *Escherichia coli*. The corresponding non-induced sample did not show any change in fluorescence colour within 30 minutes.

EXAMPLE 8

Detection of metallo-carbapenemases by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate in PBS during incubation Bacterial strains *Klebsiella pneumoniae* (VIM-1, Heidelberg) and *Pseudomonas aeruginosa* (IMP, Heidelberg) were grown over night at 37° C. in Mueller-Hinton-Broth (10 ml). To each PBS (1 ml) of fluorogenic carbapenem (100 µg) were added five drops of corresponding inoculum (McFarland 0.5). After further incubation over night at 37° C., the disappearance of the green-yellow fluorescence colour (UV light λ=366 nm) could be observed, indicating the production of carbapenemases.

EXAMPLE 9

Detection of carbapenemases by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate during incubation Bacterial strains *Escherichia coli* (ESBL-1, Heidelberg), *Escherichia coli* (ESBL-2, Heidelberg), *Escherichia coli* (Oxa-48), *Klebsiella pneumoniae* (KPC-2, Heidelberg) *Klebsiella pneumoniae* (VIM-1, Heidelberg), *Pseudomonas aeruginosa* (GES-2, Heidelberg), *Pseudomonas aeruginosa* (IMP, Heidelberg) and *Pseudomonas aeruginosa* (VIM-2, Heidelberg) were grown over night at 37° C. in Mueller-Hinton-Broth (10 ml). To each sample (1 ml, McFarland 0.5) was added fluorogenic carbapenem (100 µg). After further incubation over night at 37° C., the disappearance of the green-yellow fluorescence colour (UV light λ=366 nm)

could be observed for each carbapenemase-producing strain. The corresponding ESBL-producers did not show any change in colour.

EXAMPLE 10

Detection of carbapenemases by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate during optimized incubation Bacterial strains *Escherichia coli* (ESBL-1, Heidelberg), *Escherichia coli* (ESBL-2, Heidelberg), *Escherichia coli* (Oxa-48), *Klebsiella pneumoniae* (KPC-2, Heidelberg) *Klebsiella pneumoniae* (VIM-1, Heidelberg), *Pseudomonas aeruginosa* (GES-2, Heidelberg), *Pseudomonas aeruginosa* (IMP, Heidelberg), *Pseudomonas aeruginosa* (VIM-2, Heidelberg) were incubated for 6 h at 37° C. (220 rpm) in Mueller-Hinton-Broth (10 ml) using 45-ml-Falcon-tubes. To each sample (1 ml) was added fluorogenic carbapenem (100 µg) using 15-ml-Falcon-tubes. After further incubation over night at 37° C., the disappearance of the green-yellow fluorescence colour ($\lambda$=366 nm) could be observed for each carbapenemase-producing strain. The corresponding ESBL-producers did not show any change in fluorescence colour.

EXAMPLE 11

Detection of carbapenemases by fluorogenic potassium-(4S,5R,6S)-3-(4-acetyl-phenyl)-6-((1'R)-hydroxy-ethyl)-4-methyl-7-oxo-1-aza-bicyclo[3.2.0]hept-2-ene-2-carboxylate during chemical lysis Bacterial strains *Pseudomonas aeruginosa* DSM 1117 (no resistance), *Pseudomonas aeruginosa* (VIM-2, Heidelberg) and *Klebsiella pneumoniae* (KPC-2, Heidelberg) were incubated over night at 37° C. on Mueller-Hinton-Agar plates. A sample of each strain was suspended (McFarland 10) in primary-amine-free buffer solution (1 ml) of a detergent from Merck (Germany). Fluorogenic carbapenem (100 µg) was added. After further incubation for 6 h at 37° C., the disappearance of the green-yellow fluorescence colour ($\lambda$=366 nm) could be observed for both carbapenemase-producing strains. The corresponding sample of *Pseudomonas aeruginosa* DSM 1117 did not show any change in fluorescence colour.

The invention claimed is:
1. A method for detection of bacterial carbapenemase, the method comprising:
contacting a fluorescent or chromogenic carbapenem of formula I

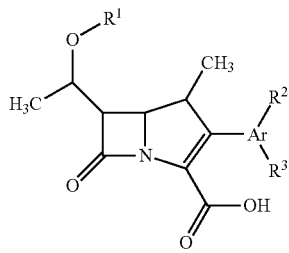

and/or its salts, wherein $R^1$ is selected from hydrogen or alkyl and acyl, each with 1 to 6 carbon atoms and wherein Ar is a mono or disubstituted carbocyclic aromatic or an optionally mono or disubstituted heterocyclic aromatic group wherein the carbocyclic aromatic moiety is monocyclic, bicyclic or tricyclic with 6 to 14 carbon atoms and the heterocyclic aromatic moiety is monocyclic, bicyclic or tricyclic and contains 1 to 13 carbon atoms and contains 1 to 5 hetero atoms, which are selected, independently from each other, from oxygen, nitrogen or sulphur and wherein the substituents $R^2$ and $R^3$ of the aromatic parts Ar are selected, independently from each other, from hydrogen, amino, hydroxy, oxo, fluoro, chloro, bromo, nitro, cyano, carboxy, carbamoyl, sulphamoyl, amidino, guanidino, sulfo, or alkyl, alkoxy, acyl, acylamino, monoalkylamino, dialkylamino, trialkylammonium, N,N-dialkylcarbamoyl, N-alkylcarbamoyl and alkoxycarbonyl, each with 1 to 6 carbon atoms; wherein at least one of $R^2$ and $R^3$ is an electron withdrawing group when Ar is a carbocyclic aromatic group; and wherein $R^2$ and $R^3$ are not both hydrogen when Ar is a carbocyclic aromatic group with a bacterium or a preparation obtained by lysis of at least one bacterial species; and detecting a change in color or fluorescence;
wherein the change in color or fluorescence is indicative of the presence of bacterial carbapenemase.

2. The method of claim 1, wherein $R^1$ is selected from hydrogen or alkyl and acyl, each with 1 to 6 carbon atoms and wherein Ar is a mono or disubstituted carbocyclic aromatic or an optionally mono or disubstituted heterocyclic aromatic group wherein the carbocyclic aromatic group Ar is selected from phenyl, 1-biphenyl-2-yl or 1-biphenyl-4-yl and wherein the heterocyclic aromatic group is selected from 2-pyridyl, 4-pyridyl or 2-pyrimidyl and wherein the substituents $R^2$ and $R^3$ of the aromatic parts Ar are selected, independently from each other, from hydrogen, amino, hydroxy, oxo, fluoro, chloro, bromo, nitro, cyano, carboxy, carbamoyl, sulphamoyl, amidino, guanidino, sulfo, or alkyl, alkoxy, acyl, acylamino, monoalkylamino, dialkylamino, trialkylammonium, N,N-dialkylcarbamoyl, N-alkylcarbamoyl and alkoxycarbonyl, each with 1 to 6 carbon atoms.

3. The method of claim 1, wherein $R^1$ is selected from hydrogen or acetyl and wherein Ar is phenyl or 1-biphenyl-4-yl, $R^2$ is hydrogen and $R^3$ is 4-acetyl or 4'-acetyl.

4. The method of claim 1, wherein microbial carbapenem resistance or the presence of bacterial carbapenemase is detected by monitoring the disappearance of fluorescence upon β-lactam hydrolysis.

5. The method of claim 1, wherein the compound of Formula I, a nutrition medium, and at least one bacterial species, are incorporated in a diluent.

6. The method of claim 1, wherein the compound of Formula I, an ionic or non-ionic detergent, and at least one bacterial species, are incorporated in a diluent.

7. The method of claim 1, wherein the compound of Formula I and a preparation obtained by lysis of at least one bacterial species are incorporated in a diluent.

8. The method of claim 1, wherein the intensity of color or fluorescence of a compound is monitored in a diluent by vision or by photoelectronic devices.

9. The method of claim 1, the method comprising:
contacting a fluorescent or chromogenic carbapenem of formula I

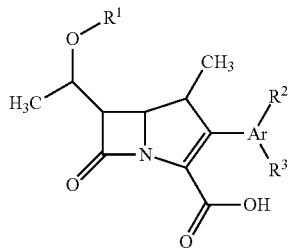

and/or its salts, wherein $R^1$ is selected from hydrogen or alkyl and acyl, each with 1 to 6 carbon atoms and wherein Ar is a mono or disubstituted carbocyclic aromatic or an optionally mono or disubstituted heterocyclic aromatic group wherein the carbocyclic aromatic moiety is monocyclic, bicyclic or tricyclic with 6 to 14 carbon atoms and the heterocyclic aromatic moiety is monocyclic, bicyclic or tricyclic and contains 1 to 13 carbon atoms and contains 1 to 5 hetero atoms, which are selected, independently from each other, from oxygen, nitrogen or sulphur and wherein the substituents $R^2$ and $R^3$ of the aromatic parts Ar are selected, independently from each other, from hydrogen, amino, hydroxy, oxo, fluoro, chloro, bromo, nitro, cyano, carboxy, carbamoyl, sulphamoyl, amidino, guanidino, sulfo, or alkyl, alkoxy, acyl, acylamino, monoalkylamino, dialkylamino, trialkylammonium, N,N-dialkylcarbamoyl, N-alkylcarbamoyl and alkoxycarbonyl, each with 1 to 6 carbon atoms; wherein at least one of $R^2$ and $R^3$ is an electron withdrawing group when Ar is a carbocylic aromatic group;

and wherein $R^2$ and $R^3$ are not both hydrogen when Ar is a carbocyclic aromatic group with a known or suspected carbapenemase inhibitor in the presence of (i) at least one carbapenemase producing bacterial species, or (ii) a preparation obtained by lysis of a carbapenemase producing bacterial species; and detecting a change in color or fluorescence;
wherein the change in color or fluorescence is indicative of inhibition of carbapenemase by the known or suspected carbapenemase inhibitor.

10. The method of claim 9, wherein $R^1$ is selected from hydrogen or alkyl and acyl, each with 1 to 6 carbon atoms and wherein Ar is a mono or disubstituted carbocyclic aromatic or an optionally mono or disubstituted heterocyclic aromatic group wherein the carbocyclic aromatic group Ar is selected from phenyl, 1-biphenyl-2-yl or 1-biphenyl-4-yl and wherein the heterocyclic aromatic group is selected from 2-pyridyl, 4-pyridyl or 2-pyrimidyl and wherein the substituents $R^2$ and $R^3$ of the aromatic parts Ar are selected, independently from each other, from hydrogen, amino, hydroxy, oxo, fluoro, chloro, bromo, nitro, cyano, carboxy, carbamoyl, sulphamoyl, amidino, guanidino, sulfo, or alkyl, alkoxy, acyl, acylamino, monoalkylamino, dialkylamino, trialkylammonium, N,N-dialkylcarbamoyl, N-alkylcarbamoyl and alkoxycarbonyl, each with 1 to 6 carbon atoms.

11. The method of claim 9, wherein $R^1$ is selected from hydrogen or acetyl and wherein Ar is phenyl or 1-biphenyl-4-yl, $R^2$ is hydrogen and $R^3$ is 4-acetyl or 4'-acetyl.

12. The method of claim 9, wherein the known or suspected inhibitor, a compound of Formula I, a nutrition medium, and at least one carbapenemase producing bacterial species are incorporated in a diluent.

13. The method of claim 9, wherein the known or suspected inhibitor, a compound of Formula I, and a preparation obtained by lysis of a carbapenemase producing bacterial species are incorporated in a diluent.

14. The method according to claim 9, wherein the inhibitor is a protease or a metallo protease inhibitor.

* * * * *